United States Patent
Tallarida et al.

(10) Patent No.: US 9,480,831 B2
(45) Date of Patent: Nov. 1, 2016

(54) VASCULAR ACCESS PORT

(71) Applicant: STD Med, Inc., Stoughton, MA (US)

(72) Inventors: Steven J. Tallarida, Mansfield, MA (US); Kenneth Arden Eliasen, Wrentham, MA (US)

(73) Assignee: Versago Vascular Access, Inc., West Bridgewater, MA (US)

( * ) Notice: Subject to any disclaimer, the term of this patent is extended or adjusted under 35 U.S.C. 154(b) by 150 days.

(21) Appl. No.: 13/770,732

(22) Filed: Feb. 19, 2013

(65) Prior Publication Data
US 2013/0231637 A1 Sep. 5, 2013

Related U.S. Application Data

(63) Continuation of application No. 12/631,268, filed on Dec. 4, 2009, now Pat. No. 8,377,034.

(51) Int. Cl.
*A61M 39/02* (2006.01)
*A61M 5/158* (2006.01)
*A61M 39/00* (2006.01)

(52) U.S. Cl.
CPC ......... *A61M 39/0208* (2013.01); *A61M 5/158* (2013.01); *A61M 2039/0081* (2013.01); *A61M 2039/0244* (2013.01)

(58) Field of Classification Search
CPC ............ A61M 2039/0261; A61M 2039/0267; A61M 2039/0244; A61M 2039/0081; A61M 5/158; A61M 39/0208; A61M 2039/0258; A61M 2039/0205; A61M 2039/0223
USPC ........................... 604/513, 175, 93.01, 95.01, 604/288.01–288.04, 891.1, 184, 502, 604/167.02
See application file for complete search history.

(56) References Cited

U.S. PATENT DOCUMENTS

| | | | |
|---|---|---|---|
| 491,963 A * | 2/1893 | Martinez | 431/133 |
| 3,819,282 A | 6/1974 | Schultz | |
| 4,181,132 A | 1/1980 | Parks | |
| 4,190,040 A | 2/1980 | Schulte | |
| 4,228,802 A | 10/1980 | Trott | |
| 4,445,896 A | 5/1984 | Gianturco | |
| 4,543,088 A | 9/1985 | Bootman et al. | |

(Continued)

FOREIGN PATENT DOCUMENTS

WO 9701370 1/1997

OTHER PUBLICATIONS

PCT International Search Report dated Nov. 21, 2001 issued in PCT Application No. PCT/US01/13749, 4 pages.

(Continued)

*Primary Examiner* — Imani Hayman
*Assistant Examiner* — Hamza Darb
(74) *Attorney, Agent, or Firm* — Grossman Tucker Perreault & Pfleger PLLC

(57) ABSTRACT

An access port, wherein the access port may include a body having an exterior surface and a chamber defined therein, a bore defined in the body providing fluid communication between the chamber and the exterior surface, a needle in fluid communication with the chamber, a passage defined in the body providing communication between the chamber and the exterior surface, a seal secured within the passage, and an actuator in communication with the needle, configured to move the needle relative to the passage or move the passage relative to the needle.

67 Claims, 12 Drawing Sheets

(56) References Cited

U.S. PATENT DOCUMENTS

| | | |
|---|---|---|
| 4,576,595 A | 3/1986 | Aas et al. |
| 4,673,394 A | 6/1987 | Fenton, Jr. et al. |
| 4,692,146 A | 9/1987 | Hilger |
| 4,710,167 A | 12/1987 | Lazorthes |
| 4,760,837 A | 8/1988 | Petit |
| 4,781,680 A | 11/1988 | Redmond et al. |
| 4,802,885 A | 2/1989 | Weeks et al. |
| 4,840,615 A | 6/1989 | Hancock et al. |
| 4,892,518 A | 1/1990 | Cupp et al. |
| 4,904,241 A | 2/1990 | Bark |
| 4,929,236 A | 5/1990 | Sampson |
| 5,006,115 A | 4/1991 | McDonald |
| 5,041,098 A | 8/1991 | Loiterman et al. |
| 5,084,015 A | 1/1992 | Moriuchi |
| 5,137,529 A | 8/1992 | Watson et al. |
| 5,203,771 A | 4/1993 | Melker et al. |
| 5,213,574 A | 5/1993 | Tucker |
| 5,215,530 A | 6/1993 | Hogan |
| 5,234,406 A | 8/1993 | Drasner et al. |
| 5,281,199 A | 1/1994 | Ensminger et al. |
| 5,295,658 A | 3/1994 | Atkinson et al. |
| 5,306,255 A | 4/1994 | Haindl |
| 5,318,545 A | 6/1994 | Tucker |
| 5,332,398 A | 7/1994 | Miller et al. |
| 5,337,756 A * | 8/1994 | Barbier ............... A61B 5/1444 600/576 |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard |
| 5,387,192 A | 2/1995 | Glantz et al. |
| 5,391,801 A | 2/1995 | Sato et al. |
| 5,399,168 A | 3/1995 | Wadsworth, Jr. et al. |
| 5,417,656 A | 5/1995 | Ensminger et al. |
| 5,476,460 A | 12/1995 | Montalvo |
| 5,520,643 A | 5/1996 | Ensminger et al. |
| 5,527,278 A | 6/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,613,945 A | 3/1997 | Cai et al. |
| 5,637,088 A | 6/1997 | Wenner et al. |
| 5,647,855 A | 7/1997 | Trooskin |
| 5,695,490 A | 12/1997 | Flaherty et al. |
| 5,702,413 A | 12/1997 | Lafontaine |
| 5,704,915 A | 1/1998 | Melsky et al. |
| 5,718,682 A | 2/1998 | Tucker |
| 5,718,692 A | 2/1998 | Schon et al. |
| 5,792,104 A | 8/1998 | Speckman et al. |
| 5,792,123 A | 8/1998 | Ensminger |
| 5,797,879 A | 8/1998 | DeCampli |
| 5,833,654 A | 11/1998 | Powers et al. |
| 5,836,935 A | 11/1998 | Ashton et al. |
| 5,843,069 A | 12/1998 | Butler et al. |
| 5,848,989 A | 12/1998 | Villani |
| 5,931,801 A | 8/1999 | Burbank et al. |
| 5,951,512 A | 9/1999 | Dalton |
| 5,954,691 A | 9/1999 | Prosl |
| 5,989,206 A | 11/1999 | Prosl et al. |
| 6,007,516 A | 12/1999 | Burbank et al. |
| 6,030,397 A | 2/2000 | Monetti et al. |
| 6,039,712 A | 3/2000 | Fogarty et al. |
| 6,113,572 A | 9/2000 | Gailey et al. |
| 6,190,352 B1 | 2/2001 | Haarala et al. |
| 6,213,973 B1 | 4/2001 | Eliasen et al. |
| 6,478,783 B1 | 11/2002 | Moorehead |
| 6,527,754 B1 | 3/2003 | Tallarida et al. |
| 6,962,577 B2 | 11/2005 | Tallarida et al. |
| 7,056,316 B1 * | 6/2006 | Burbank et al. ............ 604/891.1 |
| 7,351,233 B2 | 4/2008 | Parks |
| 7,452,354 B2 | 11/2008 | Bright et al. |
| 7,713,251 B2 | 5/2010 | Tallarida et al. |
| 7,803,143 B2 | 9/2010 | Tallarida et al. |
| 7,811,266 B2 | 10/2010 | Eliasen |
| 8,182,453 B2 | 5/2012 | Eliasen |
| 8,409,153 B2 | 4/2013 | Tallarida et al. |
| 8,529,525 B2 | 9/2013 | Gerber et al. |
| 2003/0109837 A1 | 6/2003 | McBride-Sakal |
| 2004/0097930 A1 | 5/2004 | Justis et al. |
| 2004/0158207 A1 * | 8/2004 | Hunn ................... A61M 5/158 604/164.01 |
| 2005/0014993 A1 | 1/2005 | Mische |
| 2005/0209619 A1 | 9/2005 | Johnson et al. |
| 2006/0004325 A1 * | 1/2006 | Hamatake et al. ............. 604/43 |
| 2006/0178648 A1 | 8/2006 | Barron et al. |
| 2006/0224129 A1 | 10/2006 | Beasley et al. |
| 2007/0078432 A1 | 4/2007 | Halseth et al. |
| 2007/0233019 A1 * | 10/2007 | Forsell ..................... 604/288.03 |
| 2007/0265595 A1 | 11/2007 | Miyamoto et al. |
| 2008/0039820 A1 | 2/2008 | Sommers et al. |
| 2008/0243106 A1 | 10/2008 | Coe et al. |
| 2008/0262475 A1 | 10/2008 | Preinitz |
| 2011/0137288 A1 | 6/2011 | Tallarida et al. |
| 2012/0209180 A1 * | 8/2012 | Gray et al. ................... 604/131 |
| 2012/0232501 A1 | 9/2012 | Eliasen |
| 2013/0218103 A1 | 8/2013 | Tallarida et al. |
| 2013/0226101 A1 | 8/2013 | Westcott |
| 2013/0231637 A1 | 9/2013 | Tallarida et al. |

OTHER PUBLICATIONS

PCT Written Opinion dated Dec. 19, 2002 issued in PCT Application PCT/US01/13749, 5 pages.
PCT Preliminary Examination Report dated May 28, 2003 issued in PCT Application PCT/US01/13749, 2 pages.
European Examination Report dated Jul. 30, 2003 issued in European Patent Application No. 99 964 086.5, 5 pages.
U.S. Office Action dated Aug. 27, 2003 issued in U.S. Appl. No. 09/842,458, 8 pages.
U.S. Office Action dated Dec. 23, 2003 issued in U.S. Appl. No. 09/842,458, 7 pages.
European Examination Report dated Mar. 9, 2004 issued in European Patent Application No. 99 964 086.5, 4 pages.
U.S. Notice of Allowance dated Oct. 15, 2004 issued in U.S. Appl. No. 09/842,458, 7 pages.
Australian Examination Report dated Jan. 21, 2005 issued in Australian Patent Application No. 2001257388, 2 pages.
U.S. Notice of Allowance dated Feb. 24, 2005 issued in U.S. Appl. No. 09/842,458, 6 pages.
European Examination Report dated Mar. 1, 2005 issued in European Patent Application No. 99 964 086.5, 4 pages.
European Examination Report dated Mar. 30, 2005 issued in European Patent Application No. 99 964 086.5, 3 pages.
European Decision to Refuse dated Dec. 15, 2005 issued in European Patent Application No. 99 964 086.5, 9 pages.
U.S. Office Action dated Feb. 14, 2007 issued in U.S. Appl. No. 10/890,909, 12 pages.
U.S. Office Action dated Apr. 11, 2007 issued in U.S. Appl. No. 10/931,890, 7 pages.
U.S. Office Action dated Sep. 13, 2007 issued in U.S. Appl. No. 10/890,909, 11 pages.
U.S. Office Action dated Sep. 13, 2007 issued in U.S. Appl. No. 10/931,890, 7 pages.
Canadian Office Action dated Oct. 16, 2007 issued in Canadian Patent Application No. 2,407,643, 2 pages.
U.S. Office Action dated Feb. 21, 2008 issued in U.S. Appl. No. 11/269,098, 19 pages.
U.S. Office Action dated Jun. 9, 2008 issued in U.S. Appl. No. 10/931,890, 10 pages.
U.S. Office Action dated Oct. 30, 2008 issued in U.S. Appl. No. 11/269,098, 12 pages.
U.S. Office Action dated Dec. 23, 2008 issued in U.S. Appl. No. 10/931,890, 9 pages.
U.S. Office Action dated Jun. 4, 2009 issued in U.S. Appl. No. 11/269,098, 11 pages.
Supplemental European Search Report dated Jun. 10, 2009 issued in European Patent Application No. 01 930 898.0, 4 pages.

(56) References Cited

OTHER PUBLICATIONS

U.S. Office Action dated Aug. 3, 2009 issued in U.S. Appl. No. 10/931,890, 10 pages.
European Examination Report dated Oct. 2, 2009 issued in European Patent Application No. 01 930 898.0, 4 pages.
U.S. Office Action dated Mar. 3, 2010 issued in U.S. Appl. No. 11/269,098, 15 pages.
U.S. Office Action dated Feb. 17, 2011 issued in U.S. Appl. No. 12/902,839, 17 pages.
U.S. Office Action dated Oct. 17, 2011 issued in U.S. Appl. No. 12/902,839, 11 pages.
Notice of Allowance dated Feb. 1, 2012 issued in U.S. Appl. No. 12/902,839, 7 pages.
European Office Action dated Oct. 23, 2012 issued in European Patent Application No. 01 930 898.0, 4 pages.
U.S. Office Action dated Feb. 28, 2007 issued in U. S. Appl. No. 10/374,000, 8 pages.
U.S. Office Action dated Aug. 28, 2007 issued in U.S. Appl. No. 10/374,000, 8 pages.
U.S. Office Action dated Mar. 20, 2008 issued in U.S. Appl. No. 10/374,000, 7 pages.
U.S. Office Action dated Sep. 30, 2008 issued in U.S. Appl. No. 10/374,000, 8 pages.
U.S. Office Action dated May 20, 2009 issued in U.S. Appl. No. 10/374,000, 10 pages.
U.S. Office Action dated Oct. 23, 2014 issued in U.S. Appl. No. 13/477,997, 14 pages.
U.S. Office Action dated Aug. 10, 2015, issued in U.S. Appl. No. 14/231,392, 24 pages.
International Search Report and Written Opinion dated Jul. 10, 2015, issued in PCT Patent Application No. PCT/US2015/024256, 10 pages.
International Search Report and Written Opinion dated Jul. 2, 2015, issued in PCT Patent Application No. PCT/US2015/023590, 11 pages.
International Search Report and Written Opinion dated Feb. 26, 2016, issued in PCT Patent Application Serial No. PCT/US2015/066934, 11 pages.
International Search Report and Written Opinion dated Mar. 7, 2016, issued in PCT Patent Application U.S. Appl. No. PCT/US2015/066778, 9 pages.
Access technologies, The V-A-Pu . . . Vascular Access and Beyond, downloaded from Internet Jul. 28, 2009, http://www.norfolkaccess.com/VAPs.html, 4 pages.
SyncMedical, Innovative Surgical Devices, Primo Port Products, downloaded from Internet Jul. 28, 2009, http://www.syncmedical.com/primo-port, 2 pages.
Final Office Action dated Mar. 22, 2016, issued in U.S. Appl. No. 14/231,392, 22 pages.

* cited by examiner

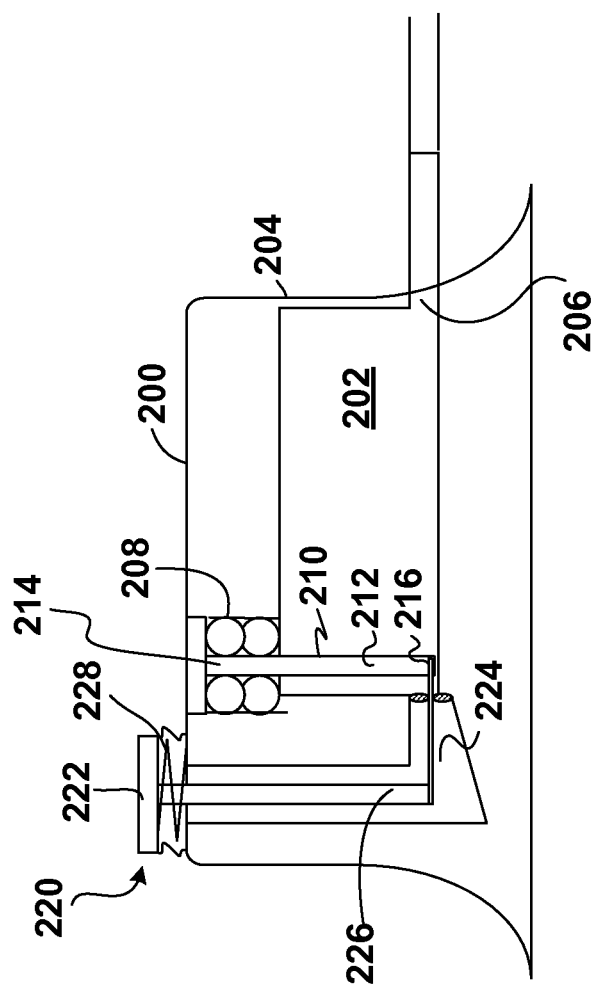

VASCULAR ACCESS PORT

CROSS REFERENCE TO RELATED APPLICATIONS

This application is a continuation of U.S. patent application Ser. No. 12/631,268 (now U.S. Pat. No. 8,377,034), filed Dec. 4, 2009, the entire disclosure of which is incorporated herein by reference.

FIELD OF THE INVENTION

The present invention relates generally to vascular access port and, in particular, to a sub-cutaneous vascular access port that may include a needle that penetrates the skin, wherein the needle may extend or retract from the housing, or the housing may expand and/or collapse around the needle.

BACKGROUND

Hematology patients, oncology patients, hemodialysis patients and other patients may be subject to frequent infusion treatments delivering pharmaceuticals, blood, nutrients, contrasting agents and other compositions. Frequent "needle sticks" and the duration of infusion time may make receiving such treatments uncomfortable. Vascular access ports are medical devices that may be inserted beneath the skin and may reduce the discomfort associated with such treatments. A port may include an access point, such as a septum, into which a needle may be inserted. A port may also include a catheter, which may be inserted into a vein, such as a jugular vein, subclavian vein or superior vena cava. The septum may be formed of a self-healing silicone material that may be punctured multiple times with a relatively low loss in its integrity. However, a clinician needs to properly target the access port and a risk of infection may exist as a needle extending into the skin may drag bacteria from the skin into the port.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein:

FIG. 2a illustrates a cross-sectional view of an example of a vascular access port contemplated herein, with the needle in the retracted position;

DETAILED DESCRIPTION

Figure 1A:
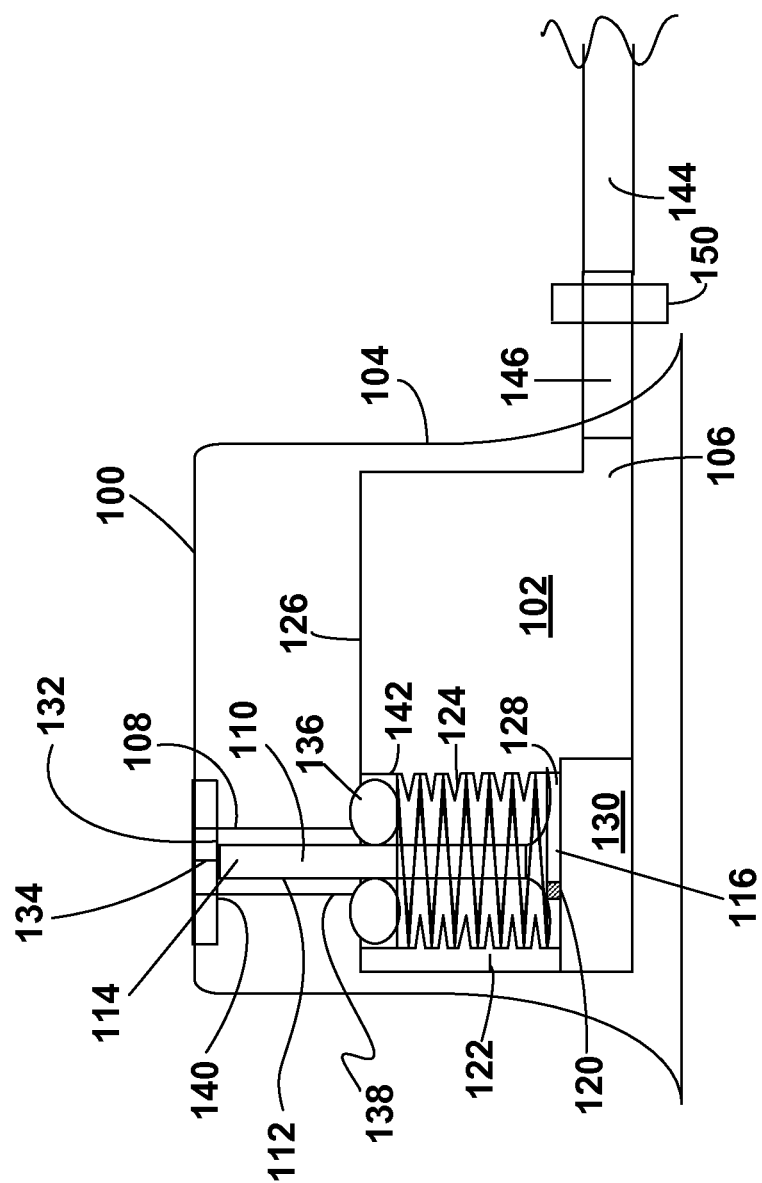
FIG. 1a illustrates a cross-sectional view of an example of a vascular access port contemplated herein, with the needle in the retracted position.

It is to be understood that this disclosure is not limited in its application to the details of construction and the arrangement of components set forth in the following description or illustrated in the drawings. The embodiments herein are capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected," "coupled," and "mounted," and variations thereof herein are used broadly and encompass direct and indirect connections, couplings, and mountings. In addition, the terms "connected" and "coupled" and variations thereof are not restricted to physical or mechanical connections or couplings.

The present invention relates generally to vascular access port and, in particular, to a sub-dermal vascular access port that includes an extendable/retractable needle or a body portion that is collapsible and expandable, configured to expose the needle upon collapsing. The needle may puncture through the subject's skin, providing access to the port. A catheter or other device may be affixed to the needle to provide a composition to the subject or the needle may puncture a vial stopper and a composition stored in the vial.

Figure 1B:
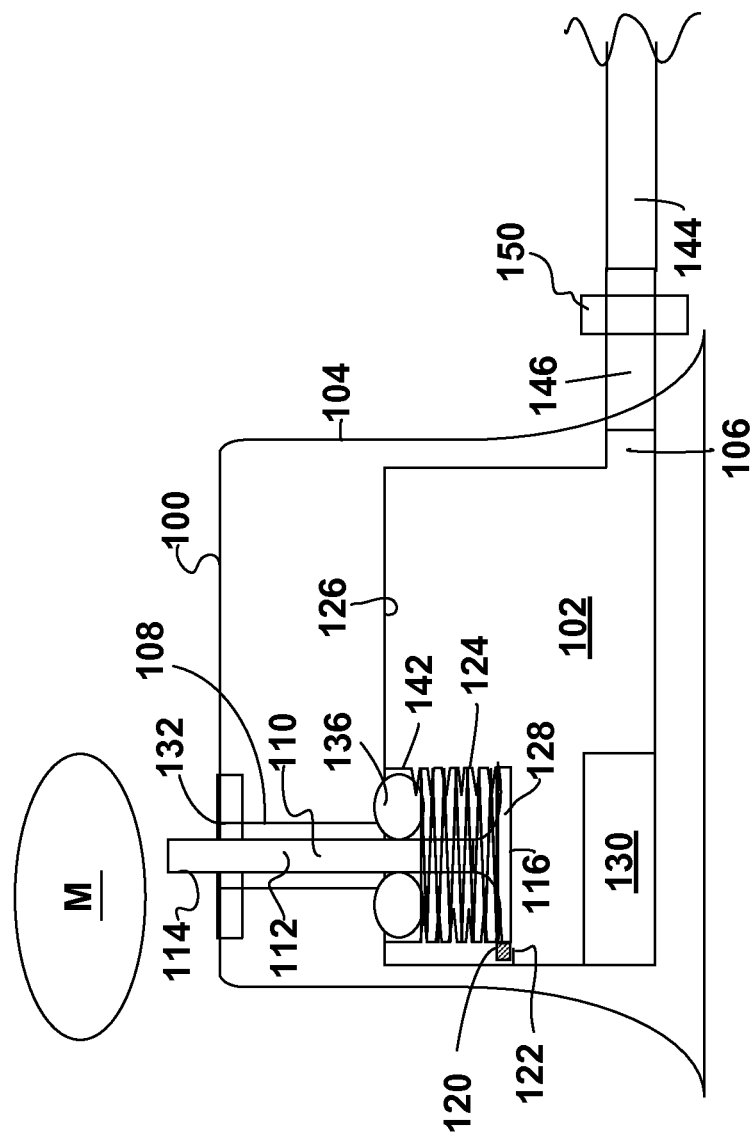
FIG. 1b illustrates a cross-sectional view of an example of a vascular access port contemplated herein, with the needle in the extended position.

FIGS. 1a and 1b illustrate examples of a vascular access port including a needle in the retracted and extended positions. The access port body 100 may generally include a chamber 102 defined in the port and an external surface 104. The port may also include a bore 106 connecting or providing fluid communication between the chamber and the external surface of the port. A passage 108 may also be provided between the chamber and an external surface of the port. A needle 110 may be positioned within the passage 108 and may extend and/or retract from the body relative to a seal (or septum described below). The needle 110 may include a shaft 112, a distal end 114 and a proximal end 116. In addition, the needle 110 may be made of a ferromagnetic material, or may include a ferromagnetic material at the distal end 114.

To extend the needle, a magnet M may be passed over the needle or may be positioned on the device to which the needle may attach. The needle, being attracted to the magnet may extend from the access port towards the magnet. In some examples, rotation of the needle may lock the needle in place. For example, the proximal end of the needle may include a projection 120 that may slide into a catch or channel 122 provided in the chamber at a given height. The needle may be retracted by releasing the magnet (i.e., moving the magnet away from the needle). In addition, the magnet may be positioned on or within the device to which the needle may be affixed to administer a given composition. For example, the magnet may be positioned proximal to the lip of a vial, near the vial stopper, or in the tip of a catheter into which the needle may be asserted.

In addition, a spring 124 may be positioned between the proximal end of the needle and a chamber wall 126 to retain the needle in the retracted position. As may be appreciated the force exerted by the spring S on the needle towards the retracted position may be less than the force exerted by the magnet M, wherein M>S. In one example, the needle may include a flare 128 at the proximal end accommodating the spring. In addition, a bumper 130 may be provided to receive the distal end of the needle in the retracted position to prevent back flow of fluid through the needle and out of the access port. The bumper may be formed into the chamber or may be adhered onto the chamber walls.

In some examples, a seal or septum 132 may be provided at the upper portion of the passage 108. This seal 132 may be provided alone or in addition to the bumper 130 provided in the chamber 102. The seal 132 may include a perforation 134 to allow the needle to more easily pass through upon application of actuation force by an actuator, which may be for example a magnetic force. In addition, an additional seal 136 may be provided to prevent backflow of the fluid in the chamber into the needle passage. It may be appreciated that further seals may be provided between the base of the passage 138 and the proximal end of the passage 140. In other embodiments, an expandable and/or collapsible sleeve 142 may be provided over the spring or needle preventing mingling of the fluids in the port with the spring surfaces or the exterior surfaces of the needle. The sleeve may be accordion like or in the shape of a bellows.

A catheter 144 may be removably attached to the access port 100 by a connector 146, or permanently attached to the access port through chemical or mechanical means, including an adhesive, ultrasonic welding, press-fits, etc. The catheter may be relatively flexible and formed of a composition such as silicone, polyurethane, or other thermoplastic elastomers. In addition, in some embodiments, a metering device 150 may be provided between the chamber and the catheter. The metering device may include a valve and allow for control of the flow rate of fluid from the port into the vascular system.

Figure 2B:
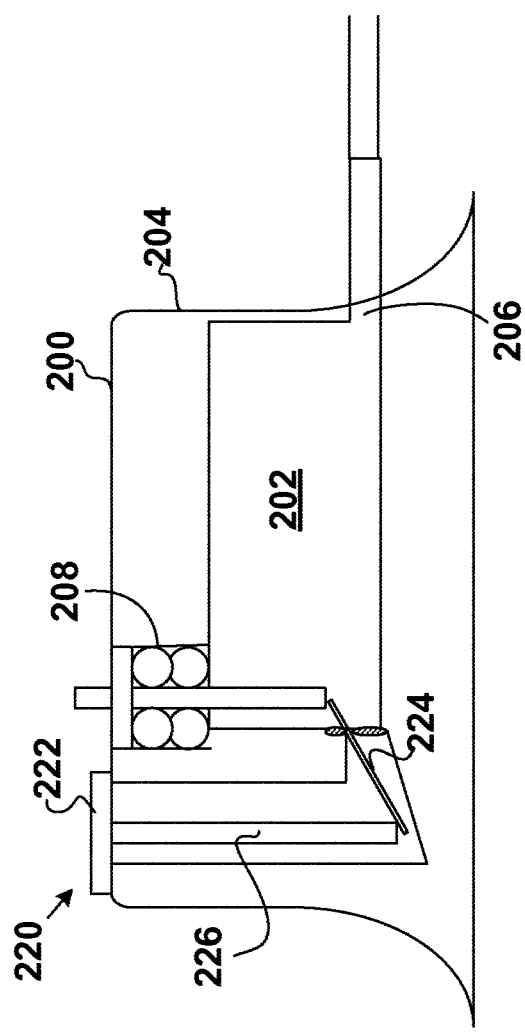
FIG. 2b illustrates a cross-sectional view of an example of a vascular access port contemplated herein, with the needle in the extended position.

In further examples, illustrated in FIGS. 2a and 2b, the vascular access port may include a retractable and extendable needle, retracted and expanded by a mechanical actuator. The access port body 200 may again generally include a chamber 202 defined in the part and an external surface 204. The port may include a bore 206 connecting or providing fluid communication between the chamber and the external surface of the port. A passage 208 to accommodate the travel of the needle 210 may be provided between the chamber and an external surface of the port. The needle 210 may include a shaft 212, a distal end 214 and a proximal end 216.

The mechanical actuator 220 may include a mechanical linkage. In one example, a button 222 may be mechanically affixed to a lever 224, which is affixed to the needle, by a first linkage 226. Upon pressing the button, the lever may rotate around a pivot point and raise the needle through the subject's skin. Other linkages may be envisioned and are not limited to the linkage herein. Furthermore, a spring 228 may be provided, such as under the button, which raises the button and thereby withdraws the needle. In other examples, the needle may be spring loaded, biasing the needle into the retracted position. The button may be directly pressed by a person providing a composition into the port. However, it may also be envisioned that the button may be pressed by pushing against it with a vial or other container including the composition to be provided to the subject.

Figure 3A:
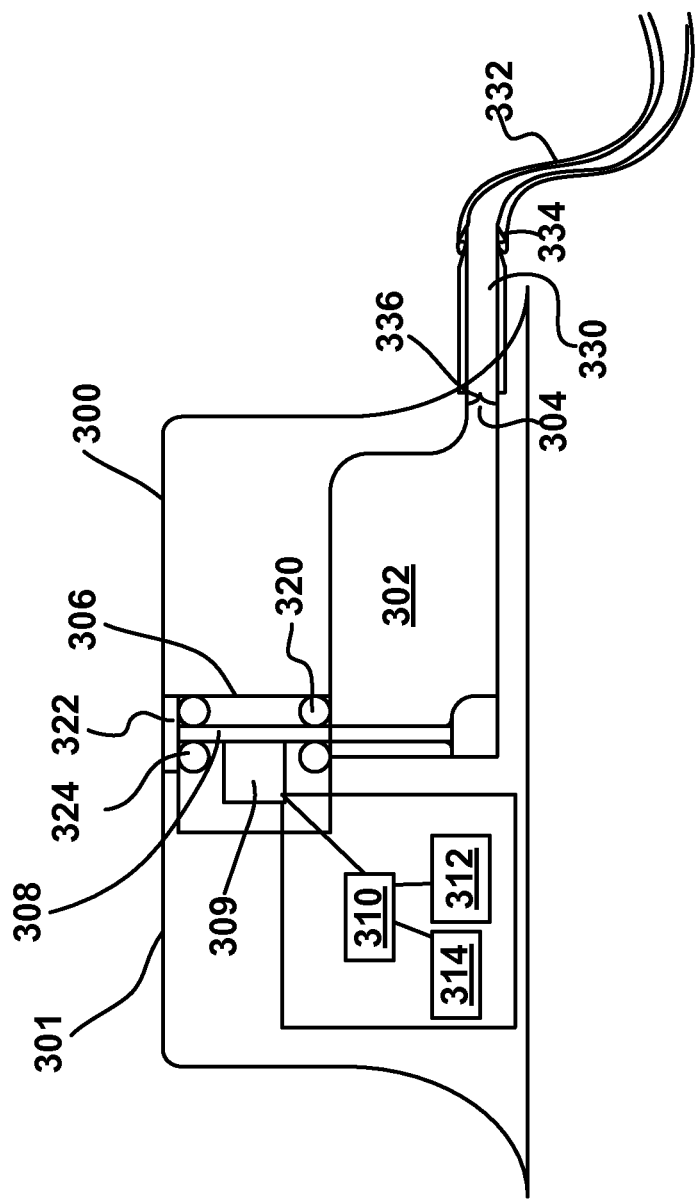
FIG. 3a illustrates a cross-sectional view of an example of a vascular access port contemplated herein, with the needle in the retracted position.
Figure 3B:
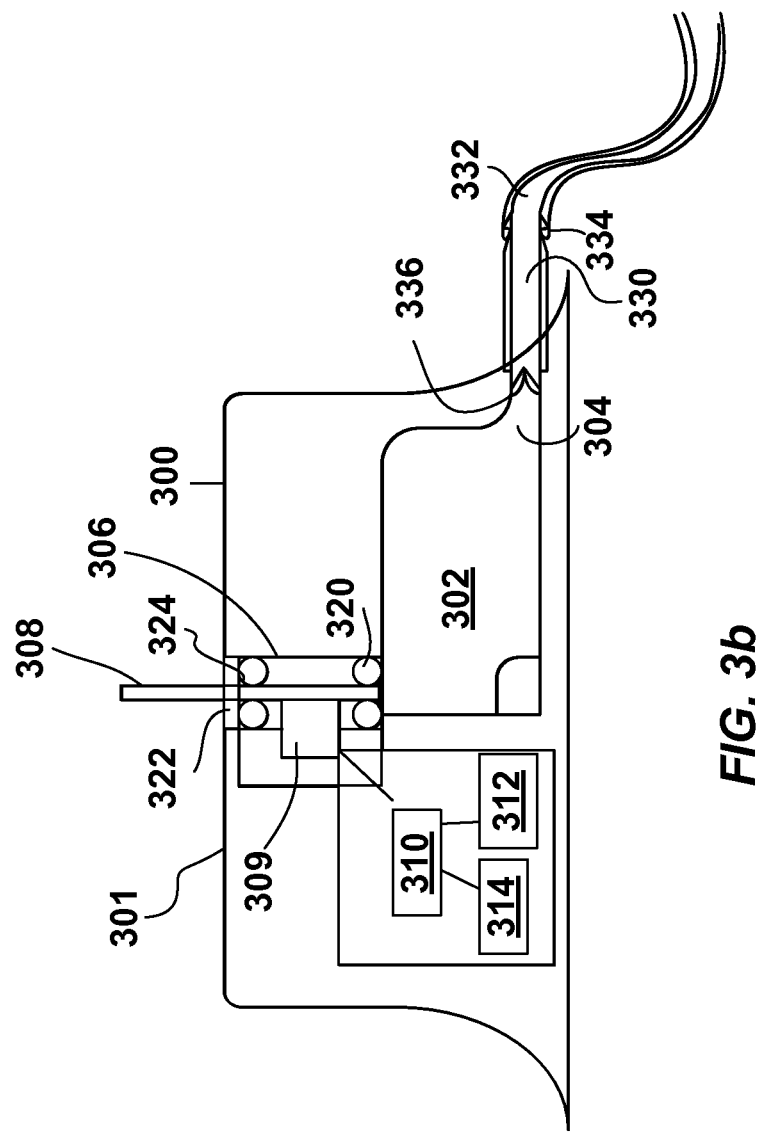
FIG. 3b illustrates a cross-sectional view of an example of a vascular access port contemplated herein, with the needle in the extended position.

In another example, as illustrated in FIGS. 3a and 3b, the vascular access port may include a needle that may be extended or retracted by an actuator that includes electrical/mechanical device. The access port body 300 may include a chamber 302 defined therein as well as a bore 304 that extends from the chamber to an exterior surface of the access port, providing communication between the interior (chamber) of the access port and the external environment. In addition, the access port may include a passage 306, which may accommodate the needle 308 as it extends or retracts with respect to a surface 301 on the body 300 of the access port.

The access port may also include a motor or other device that may extend or retract the needle. Motors may include linear piezoelectric or electromagnetic motors. In some examples, the motor may be a piezoelectric micro-motor 309. The motor may include a linear traveler, such as a shaft or translator. In some examples, the shaft or translator may interact with the needle translating the needle up and down relative to the port body. In other examples, the shaft or linear translator may be the needle, having a hollow cylinder defined therein.

In some examples, a processor 310 may be provided to power the motor and control the direction of needle travel. The processor and motor may be powered by a power supply 312. The power supply may communicate electrically either directly or indirectly with either the processor and/or motor. For example, in some cases, the processor may provide power to the motor and in other cases a transformer may be provided either between the power supply and processor and/or between the power supply and the motor.

The processor may be actuated by an activator. In some examples, a "button" or other device may be provided that, when depressed or otherwise activated, may send a signal to the processor to actuate the needle. In other examples, the port may include a communication device 314 such as a receiver or transceiver, which may include a receiver. The communication device may be configured to receive or transmit an electromagnetic indicator, such as electromagnetic waves or signals such as radio waves or optical waves, received from a wireless activator. For example, the communication device may receive radio waves from an RFID (radio frequency identification) device. The RFID device may be integrated into a tag or card that when brought into proximity with the access port may activate the actuator (i.e., the processor) and cause the needle to extend from the access port body. In another example, the communication device may detect or receive optical signals. Such signals may be in the range of 200 nm to 900 nm, including all values and increments therein, such as 200 nm to 400 nm (ultraviolet light), 380 nm to 750 nm (visible light), 750 nm to 1400 nm (infrared light). In some embodiments, the optical waves may exhibit a Fraunhofer wavelength, i.e., a wavelength not emitted by the sun, preventing accidental triggering of the device upon exposure to the sun. It may be appreciated that the radio or optical signals may be received or detected at a single wavelength or at multiple wavelengths, including 1 wavelength to 20 wavelengths and all values and increments therein. Other devices that may be used to cause the processor to actuate the motor may include wi-fi, Bluetooth or other transmitters or transceivers including transmitters, light. Furthermore, a light pen, or other light source may be an activator for the processor to actuate the motor.

The electromagnetic indicators may be provided by a transmitter or a transceiver that may include a transmitter in the activator. The electromagnetic indicators may be pulsed or otherwise manipulated to provide directions or instructions. For example, the indicators may signal for the processor to extend the needle or retract the needle. In other examples, the indicators may provide an identifier to prevent cross-talk between devices or prevent accidental extension or retraction of the needle. The activator may also include a processor for regulating the signals from the transmitter, which may be in electrical communication with the processor.

Figure 4:
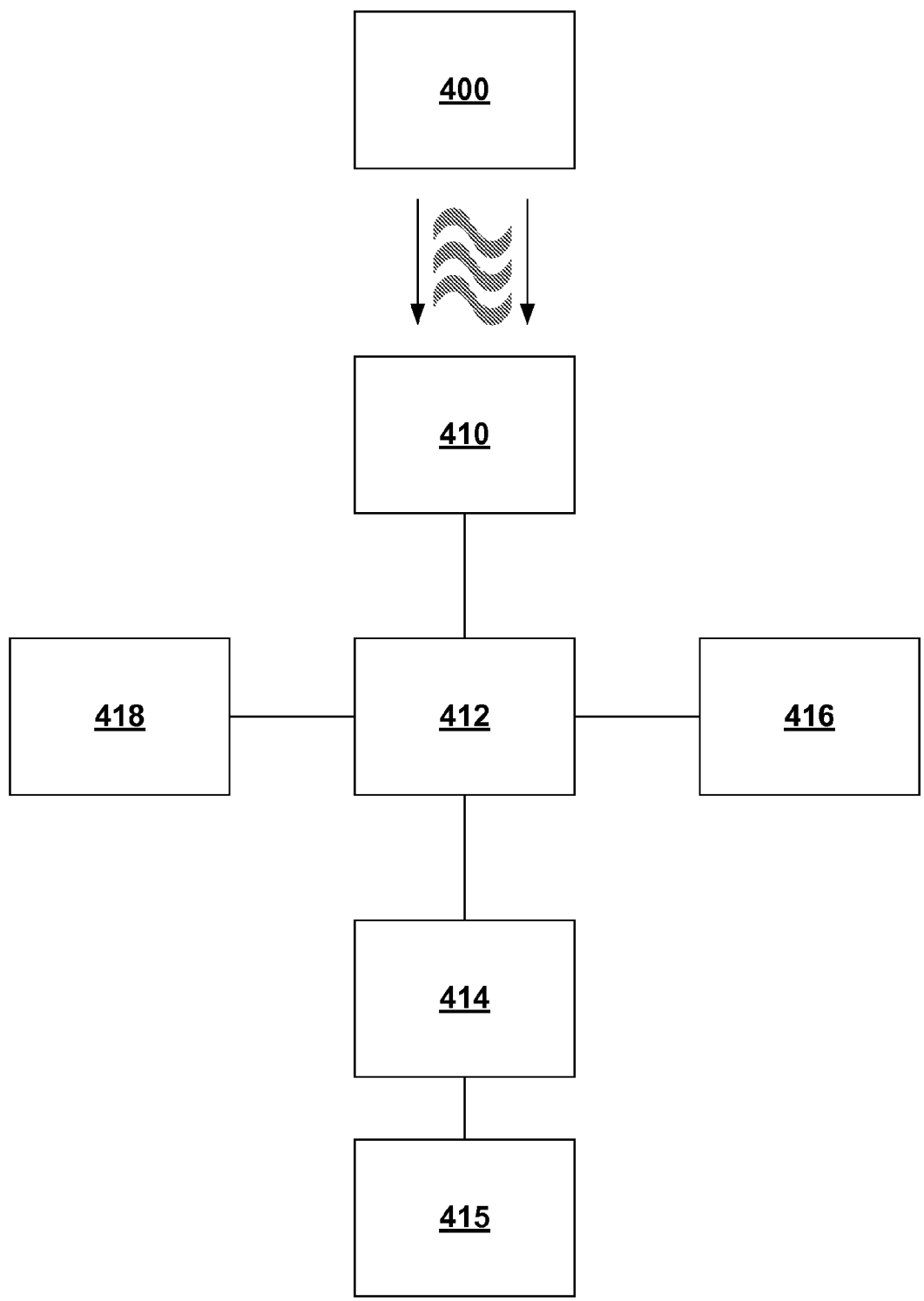
FIG. 4 illustrates a schematic of a control system for a vascular access port.

Accordingly, it may be appreciated that a system may be provided including the vascular access port and an activator. An example of such a system is illustrated in the schematic diagram of FIG. 4, wherein an activator 400 may emit various electromagnetic signals or waves. Upon receiving the electromagnetic waves, the receiver 410 may convert the waves into electrical pulses that may be communicated to the processor 412. Depending on the signals received, the processor may perform a number of functions. In some examples, the processor may actuate the motor 414 to extend or retract the needle 415. In other examples, the processor may identify the received signals as being indentifying information that correlates the activator with the access port. The processor may compare the indentifying information with a lookup table or identifying information stored in a memory device 416. If the identifying information is correct, then the processor may employ any commands that may be received from that device to extend or retract the needle. It may be appreciated that identifying information may be transmitted a single time or multiple times, such as with each command. Upon receiving a signal to actuate the motor, i.e., extend or retract the needle, the processor may send an electrical signal to the motor or provide power to the motor from the power supply 418 such that the motor will displace the linear traveler, extending or retracting the needle.

Returning again to FIGS. 3a and 3b, the body 300 may include a number of seals that may isolate the chamber and the interior of the needle. For example, a first seal or set of seals 320 may be provided where the needle extends into the chamber. The seal may prevent the composition being injected into the port from flowing back into the passage. In another example, a septum 322 may be provided at the surface 301 of the body. The needle 308 may penetrate the septum 322 when extended and the septum may prevent fluids or other contaminants from entering the port. In addition, the septum may be formed from a self healing composition, such as silicone or natural rubber. In a further example, another set of seals 324 may be provided near the surface 301 of the body, wherein the seal 324, like the septum, may prevent fluids or other contaminants from entering the port.

The port may also include a connector 330, which may connect the bore 304 leading into the chamber with a catheter 332. The connector may include barbs 334 or other mechanical interlocks to retain the catheter on the port. However, it may be appreciated that, in some examples, the catheter may be removed from the connector. In other embodiments, the catheter may be welded to the port, permanently affixing the catheter to the port.

In addition, as illustrated in the embodiment above, the chamber, e.g., chamber 302 of FIG. 3, may be defined to assume different geometries. Accordingly, rather than assuming the geometry of a rather rectangular reservoir, the chamber may assume the shape of an ellipse, oval, circle, shaft or other geometric configurations. In addition, while the needle is illustrated as being positioned on a stopper in the retracted position, it may be appreciated that the needle need not return against another object or may return against a wall of the chamber.

Furthermore, with reference to FIG. 3a and FIG. 3b, it may be appreciated that the bore may include a seal 336. The seal may allow for fluids to pass out of the bore from the chamber and into the connector and/or catheter. However, in some examples, the seal may prevent backflow from the connector and/or catheter. For example, in one embodiment, the seal may include a duckbill valve.

In a further embodiment, at least a portion of the access port body may move relative to the needle, such that the needle may be fixed with regard to the chamber but may still move relative to the septum 522. The body may therefore collapse, exposing the needle or extend to cover the needle. In one example, illustrated in FIG. 5a and FIG. 5b, the body 500 may include a first portion 540 and a second portion 542. To locate the first portion of the body relative to the second portion of the body, the first portion of the housing 540 may include a first wall 544 extending from the main segment 546 of the first portion of the body 500. In addition, the second portion 542 of the housing may include a second wall 548 and a support member 550. The first wall 544 may be received in a sliding manner between the second wall 548 and the support member 550.

Figure 5A:
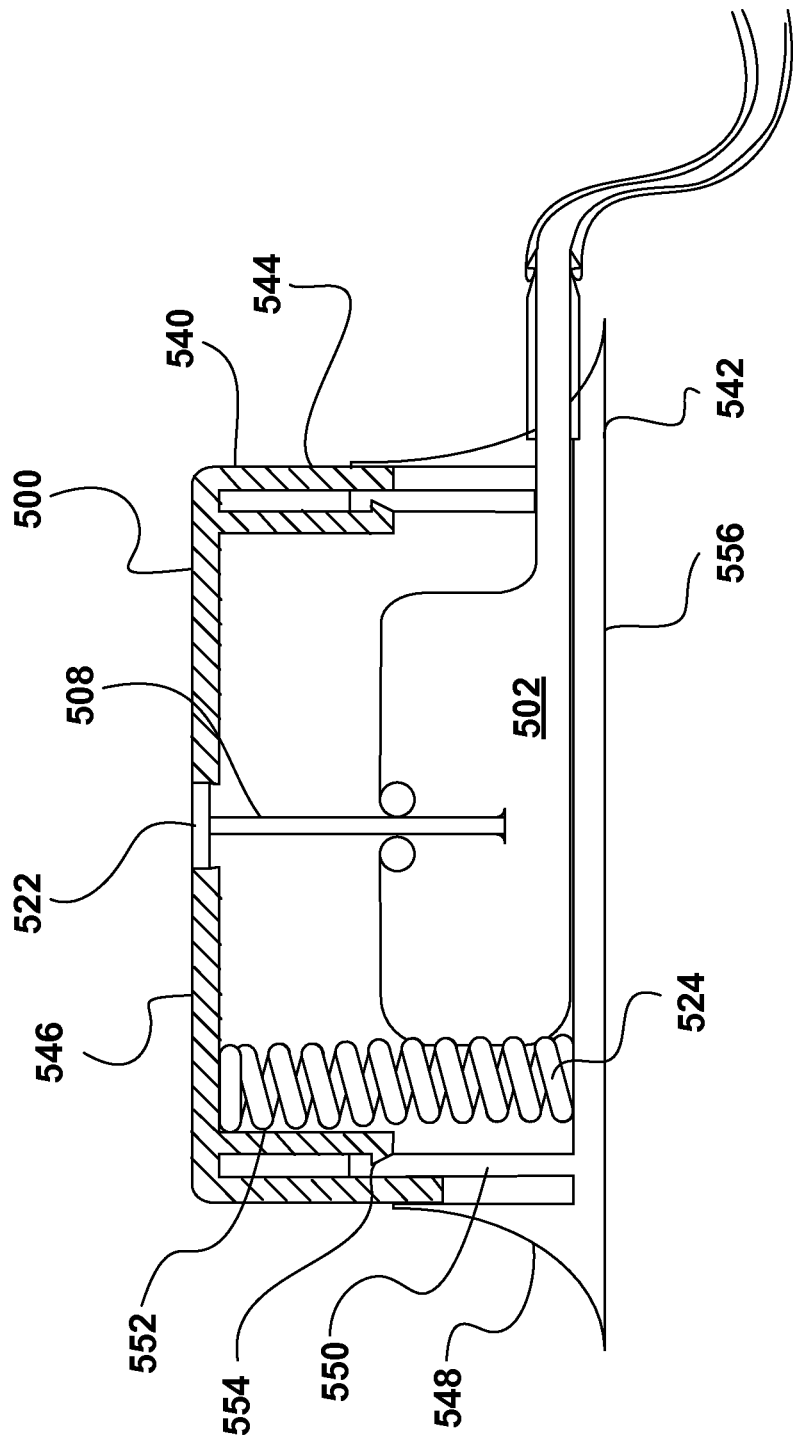
FIG. 5a illustrates a cross-sectional view of an example of a vascular access port contemplated herein, with the needle in the retracted position.

The first portion 540 may also include one or more tabbed latches 552 also extending form the main segment of the first portion around the periphery of the housing, which may hold the body in a first expanded position as illustrated in FIG. 5a. The tabbed latch may be received in a recess 554 provided by a support member 550 found in the second portion 542 of the body. When the access port body 500 is held in the first expanded position, the needle 508 may be completely or substantially contained within the access port body 500.

Figure 5B:
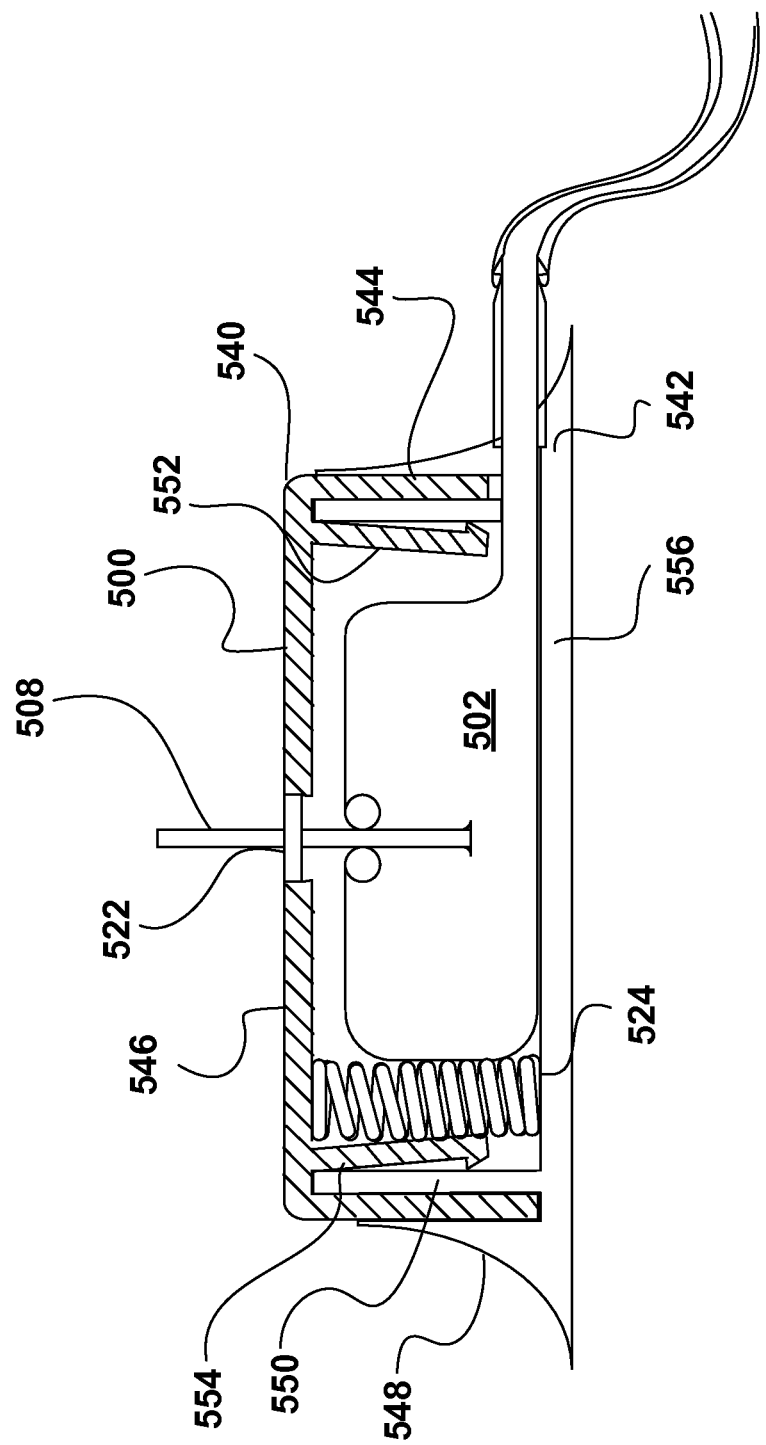
FIG. 5b illustrates a cross-sectional view of an example of a vascular access port contemplated herein, with the needle in the extended position.

When collapsed, through the application of force on the body, the needle 508 which may be held in a fixed position relative to the second portion 542 of the body may perforate and extend through the septum 522, as illustrated in FIG. 5b. In addition, the first wall 544 of the first portion may slide towards the main segment 556 of the second portion between the second wall 548 and the support member 550. The body may be maintained in a collapsed positioned through continuous application of pressure. A spring 524 may also be provided which may raise the first portion of the body 540 back to the first expanded position as illustrated in FIG. 5a.

A chamber 502 may be provided within the access port body 500 and mounted to or provided within, for example, the second portion of the body 542. In some examples, the needle 508 may be fixedly mounted to the chamber 502. While it is illustrated in FIGS. 5a and 5b that the needle may extend into the chamber 502, the needle may also be provided flush with the chamber 502. In some examples, the needle may be integrated into the chamber 502 or access port body 500. Furthermore, in some examples, the needle 508 may include threads or another mechanical interlock allowing for the needle to be removed from either the chamber 502 or access port body 500 for replacement.

Figure 6A:
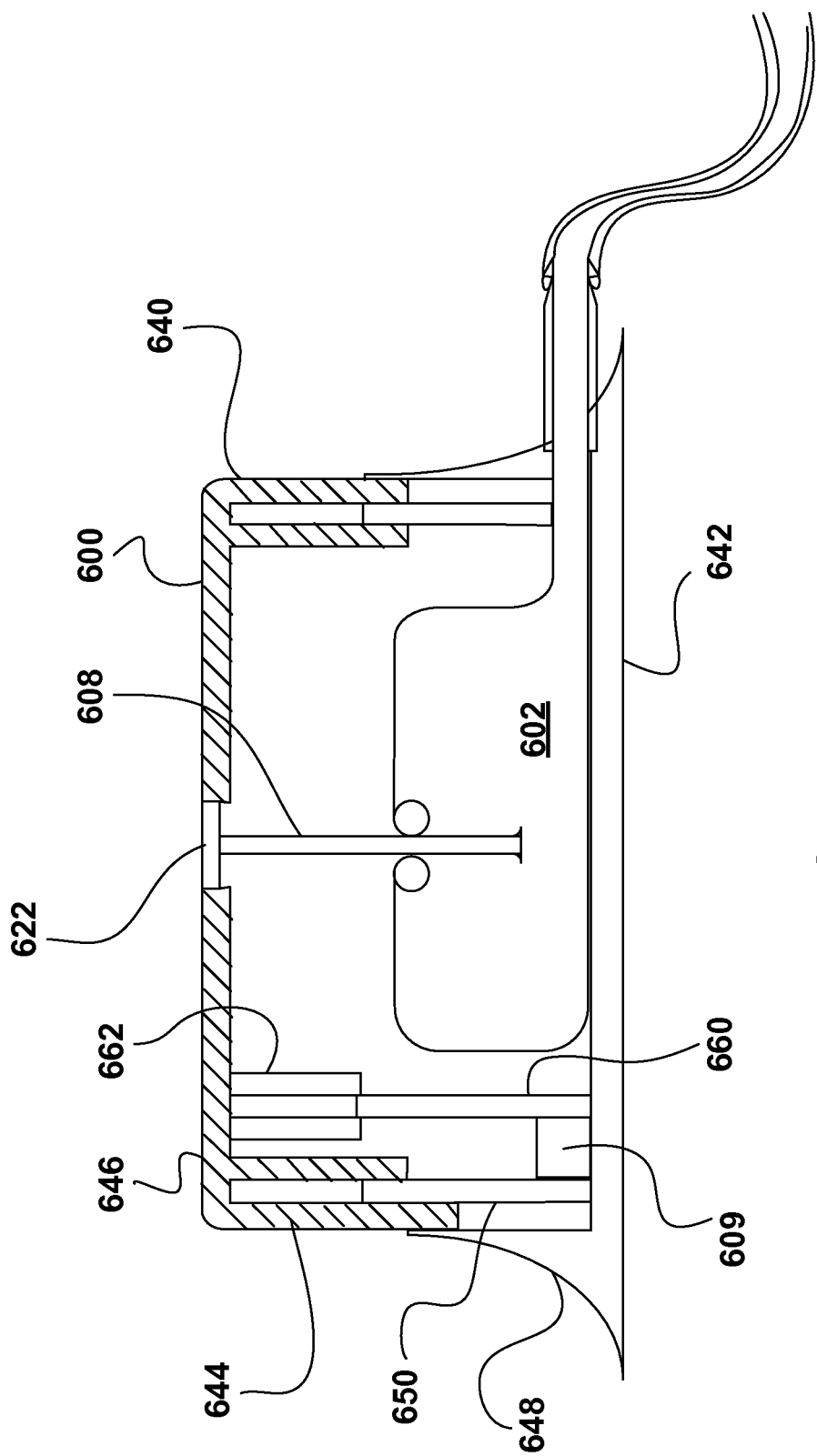
FIG. 6a illustrates a cross-sectional view of an example of a vascular access port contemplated herein, with the needle in the retracted position.
Figure 6B:
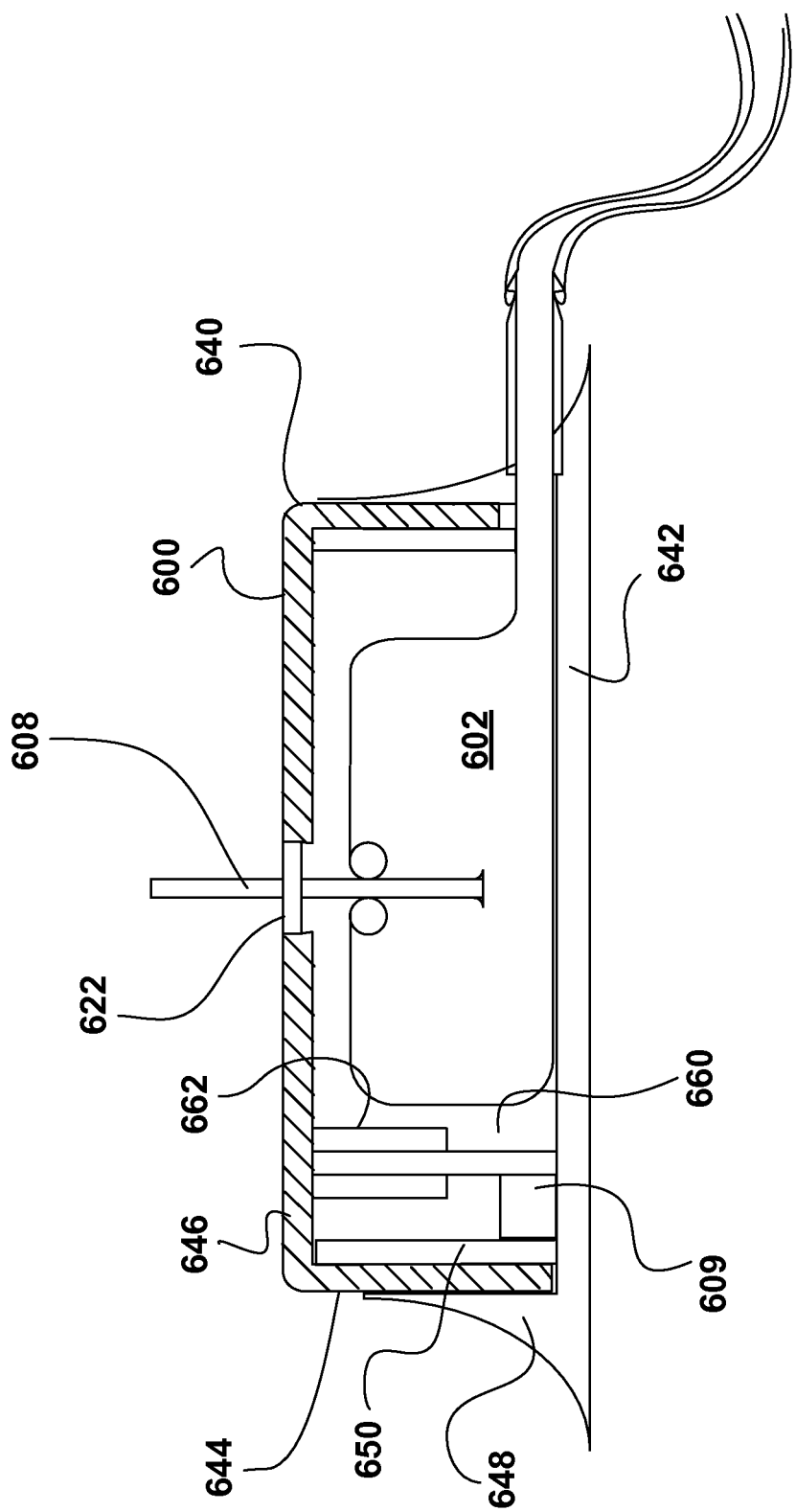
FIG. 6b illustrates a cross-sectional view of an example of a vascular access port contemplated herein, with the needle in the extended position.

FIGS. 6a and 6b illustrate an example, wherein the first and second portions 640, 642 of the access port body 600 may be extended or retracted by an actuator that includes an electrical/mechanical device. The access port may include a motor or other device that may expand or collapse the housing 609. In some examples, the motor may include a piezoelectric micro-motor 609. The motor 609 may include a linear traveler 660, such as a shaft or a translator that may interact with a cylinder 662 provided in the housing, moving the housing halves 640, 642 relative to each other. It may be appreciated that the cylinder need not be a tube having a complete wall, for example, slots may be provided in the wall. The linear traveler 660 may include, for example, a set of external threads, which may interact with a set of internal threads provided on the cylinder 662.

As the linear traveler rotates, the cylinder 662 and one of the portions, to which the cylinder is mounted may move relative to the other portion. When linear traveler rotates in one direction, the body may collapse, wherein the needle 608 may pass through the septum 622 and may be exposed. When the traveler rotates in the other direction, the body may expand, wherein the needle 608 may be pulled back through the septum 622 and covered. As illustrated, the motor is mounted the second portion and the cylinder to the first portion, but it may be appreciated that opposite situation where the motor is mounted to the first portion and the cylinder is mounted to the second portion may be provided as well. The motor may be actuated by an activator, such as a "button" or by another device, such as a wireless device as described above with reference to FIGS. 3a and 3b. Again, in one example, to locate the first portion of the housing relative to the second portion of the housing, the first portion of the body 640 may include a first wall 644 extending from the main segment 646 of the first portion or the body. In addition, the second portion 642 of the body may include a second wall 648 and a support member 650. The first wall 644 may be received in a sliding manner between the second wall 648 and the support member 650.

The needles contemplated herein, may include any hollow cylinder or shaft. The needle may include, in some examples, standard bevels, short bevels, true short bevels, etc. Furthermore, the needles may exhibit an outer diameter in the range of 0.1 mm to 4.6 mm, including all values and increments therein. In addition, the needle may exhibit an inner diameter in the range of 0.08 mm to 4.0 mm, including all values and increments therein. Furthermore, the needles may exhibit a nominal wall thickness in the range of 0.002 mm to 0.4 mm including all values and increments therein. The needles may be formed of stainless steel, ceramic composites, or other materials. In addition, the needles or the needle tips may be replaceable in case of dulling.

Figure 7A:
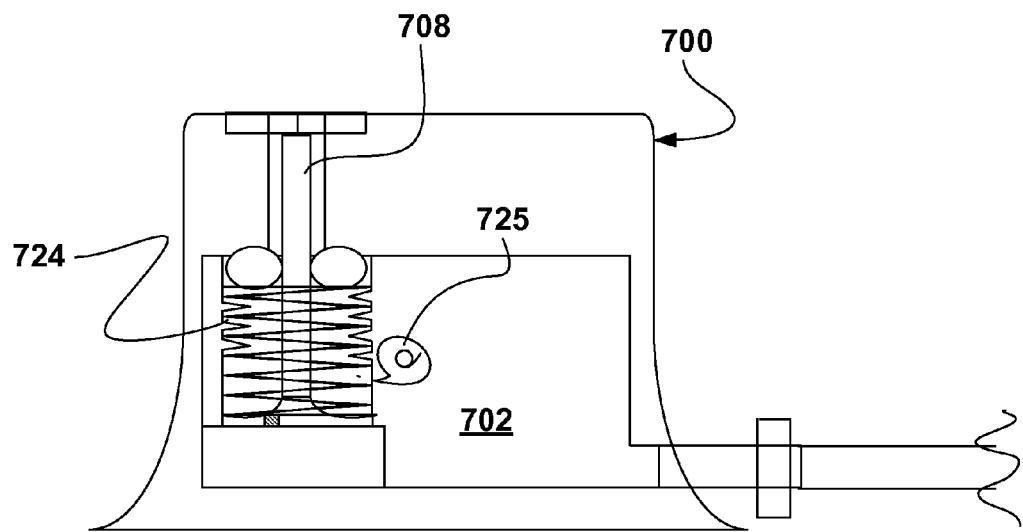
FIG. 7a illustrates a cross-sectional view of an example of a vascular access port contemplated herein, with the needle in the retracted position.
Figure 7B:
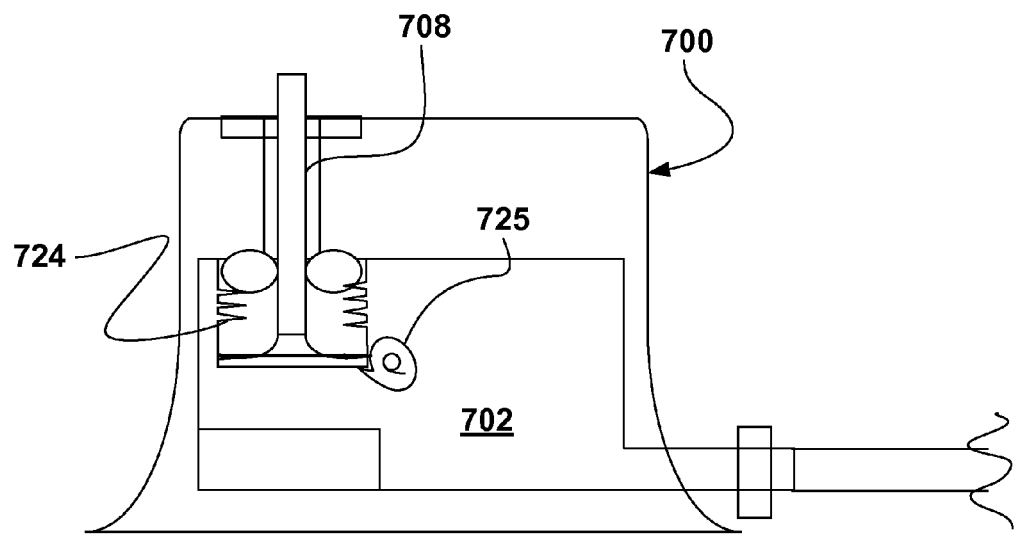
FIG. 7b illustrates a cross-sectional view of an example of a vascular access port contemplated herein, with the needle in the extended position.

As noted earlier, the needle may be positioned within the access port body in a moving relationship to the chamber or in a fixed relationship to the chamber. For example, as illustrated in FIGS. 7a and 7b, a needle 708 may be provided in moving relationship to the chamber 702. The needle may include a latching mechanism to keep the needle from moving relative to the chamber and may be activated by an actuator. Upon actuation, the needle may be lifted out of the access port body (such as by the action of a magnet) and retained in the open position by a spring loaded cam 725. The needle may be held by a spring 724 in the closed or retracted position, keeping the needle from slipping out of the access port. In other embodiments, such as illustrated in FIGS. 3a and 3b, the linear traveler provided in the motor 309 may include teeth or threads that may hold the needle 308 in place.

Accordingly, a method of injecting a composition into a subject may be provided using the access port described herein. As alluded to above, a composition may include pharmaceuticals, nutrients, contrasting agents, blood or its components, etc. Furthermore, a subject may include any vertebrate or invertebrate, including humans, other mammals, ayes, reptiles, etc. A vascular access port may be implanted into the subject and the catheter may be inserted into a vein. The needle may be extended from the port upon actuation and may puncture the skin. A composition may be introduced to the subject by either injecting the composition into the needle or otherwise introducing the needle into a container, such as through a vial stopper. Once administration of the composition is finished, the needle may be retracted or otherwise positioned back through the skin and into the port.

In another example of a method of delivering a composition utilizing a vascular access port contemplated herein, a receiver may receive or otherwise detect a first electromagnetic indicator from a transmitter, such as an activator. The indictor may be processed by the receiver to provide an electrical signal to a processor in electrical communication with the receiver. A motor may be activated by the processor once it receives a signal to activate the motor and the motor may extend or retract the needle with respect to the body of the vascular access port or the motor may collapse or expand the vascular access port with respect to the needle.

In addition, as may be appreciated herein, the actuator may be provided in direct or indirect communication with the needle and is configured to either move the needle relative to the access port body or move the access port body relative to the needle. Communication may be electrical and/or mechanical, such as that provided by magnetic fields, electrical signals, mechanical linkages or forces, provided by levers, springs, etc. Furthermore, in instances where the housing may move relative to the needle, communication may be considered indirect. It may also be appreciated that the actuator may be located outside of the housing body, located at least partially within the housing body or located completely within the housing body.

The foregoing description of several methods and embodiments has been presented for purposes of illustration. It is not intended to be exhaustive or to limit the claims to the precise steps and/or forms disclosed, and obviously many modifications and variations are possible in light of the above teaching. It is intended that the scope of the invention be defined by the claims appended hereto.

What is claimed is:

1. An access port system, comprising:
   an implantable access port to be implanted into a subject, said access port including an access port body and an access port needle, said needle contained within said access port body;
   wherein said needle is selectively disposable in an extended position and a retracted position;
   wherein said needle is coupled to said access port body in said extended position and said retracted position;
   wherein, when said needle is in said extended position, said access port is arranged such that a composition is introducible through said needle into a chamber within said access port body;
   wherein said needle is configured to be extended from within said access port body and configured to be retracted into said access port body; and wherein said needle is arranged within said access port body to penetrate outwardly through skin of said subject from within said subject when said access port is implanted in said subject.

2. The access port system of claim 1, wherein said access port includes at least one of a seal and a septum, and said needle is configured to pass through at least one of said seal and said septum.

3. The access port system of claim 1, further comprising a catheter in fluid communication with said chamber.

4. The access port system of claim 1, wherein a catheter is coupled to said access port.

5. The access port system of claim 1, wherein said needle is arranged within said access port body to penetrate outwardly through said access port body when disposed from said retracted position to said extended position.

6. The access port system of claim 1, wherein said access port body and said needle are configured such that said needle is completely containable within said access port body.

7. The access port system of claim 1, wherein said needle is arranged within said access port body to penetrate outwardly through at least one of a seal and a septum when disposed from said retracted position to said extended position.

8. The access port system of claim 1, wherein said access port body and said needle are configured such that said needle is completely contained within said access port body.

9. The access port system of claim 1, further comprising an actuator configured to move said needle.

10. The access port system of claim 9, wherein said actuator is operable to apply an actuation force to move said needle.

11. The access port system of claim 9, wherein said actuator is operable in at least one of magnetic, mechanical and electrical communication with said needle.

12. The access port system of claim 9, wherein said actuator is configured to move said needle from said retracted position to said extended position.

13. The access port system of claim 9, wherein said actuator is configured to move said needle from said extended position to said retracted position.

14. The access port system of claim 9, wherein said needle is configured to be extended from within said access port body by said actuator.

15. The access port system of claim 9, wherein said needle is configured to be retracted into said access port body by said actuator.

16. The access port system of claim 9, wherein said actuator is outside said access port.

17. The access port system of claim 9, wherein said access port includes said actuator.

18. The access port system of claim 17, wherein said actuator is at least partially contained within said access port body of said access port.

19. The access port system of claim 18, wherein said actuator is completely contained within said access port body of said access port.

20. The access port system of claim 9, wherein said actuator comprises a magnetic actuator.

21. The access port system of claim 20, wherein said magnetic actuator comprises at least one magnet configured to move said needle with a magnetic force.

22. The access port system of claim 9, wherein said actuator comprises a mechanical actuator.

23. The access port system of claim 22, wherein said mechanical actuator comprises at least one of a mechanical linkage, a lever, a spring, a pivot point and a push button.

24. The access port system of claim 23, wherein said spring comprises a coil spring.

25. The access port system of claim 23, wherein said spring is configured to move said needle towards said retracted position.

26. The access port system of claim 9, wherein said actuator comprises an electrical actuator.

27. The access port system of claim 26, wherein said electrical actuator comprises at least one of a motor, a linear traveler, a processor, a memory, a communication device, a transmitter, a receiver, a transceiver and a power supply.

28. The access port system of claim 9, wherein said actuator comprises a wireless electrical actuator which communicates wirelessly with said access port.

29. The access port system of claim 1, wherein said access port includes a mechanism to lock said needle in said extended position.

30. A method of introducing a composition into a subject, comprising:
    extending an access port needle through skin of said subject from a retracted position within an access port containing said needle positioned within said subject to an extended position such that said needle penetrates said skin from within the subject and is exposed outside said subject, wherein said access port comprises an access port body and said needle, and
    wherein said needle is selectively disposable in said extended position and said retracted position,
    wherein said needle is coupled to said access port body in said extended position and said retracted position,
    wherein, when said needle is in said extended position, said access port is arranged such that said composition is introducible through said needle into said access port,
    wherein said needle is configured to be extended from within said access port body and configured to be retracted into said access port body; and
    introducing a composition into said access port through said needle when said needle is in said extended position, and subsequently into said subject.

31. The method of claim 30 further comprising:
    retracting said needle through said skin of said subject and into said access port body after said step of introducing said composition into said access port through said needle when said needle is in said extended position, and subsequently into said subject.

32. The method of claim 30 wherein:
    said access port is attached to a catheter.

33. The method of claim 32 wherein:
    said step of introducing a composition into said access port through said needle when said needle is in said extended position, and subsequently into said subject further comprises introducing a composition into said access port through said needle when said needle is in said extended position, through said catheter, and subsequently into said subject.

34. The method of claim 33 wherein:
    said catheter is inserted into a vein of said subject.

35. The method of claim 34 further comprising:
    introducing said composition into said vein of said subject from said catheter.

36. The method of claim 35 wherein:
    said vein is a jugular vein, a subclavian vein or a superior vena cava.

37. The method of claim 35 wherein:
said composition comprises at least one of blood, a pharmaceutical, a nutrient and a contrasting agent.

38. The method of claim 30 further comprising:
collapsing said access port body while extending said needle through said skin of said subject.

39. The method of claim 38 further comprising:
expanding said access port body while retracting said needle through said skin of said subject.

40. An access port system, comprising:
an implantable access port to be implanted into a subject, said access port including an access port body and an access port needle;
wherein said needle is configured to be extended from within said access port body to an extended position and configured to be retracted into said access port body to a retracted position;
wherein, when said needle is in said retracted position, said needle is stored within said access port;
wherein, when said needle is in said extended position, said access port is arranged such that a composition is introducible through said needle to at least one of a catheter and a catheter connector of said access port; and
wherein said needle is arranged within said access port body to penetrate outwardly through skin of said subject from within said subject when said access port is implanted in said subject.

41. The access port system of claim 40, wherein said access port includes at least one of a seal and a septum, and said needle is configured to pass through at least one of said seal and said septum.

42. The access port system of claim 40, wherein the at least one catheter is coupled to said access port.

43. The access port system of claim 40, wherein said needle is arranged within said access port body to penetrate outwardly through said access port body when disposed from said retracted position to said extended position.

44. The access port system of claim 40, wherein said access port body and said needle are configured such that said needle is completely containable within said access port body.

45. The access port system of claim 40, wherein said needle is arranged within said access port body to penetrate outwardly through at least one of a seal and a septum when disposed from said retracted position to said extended position.

46. The access port system of claim 40, wherein said access port body and said needle are configured such that said needle is completely contained within said access port body.

47. The access port system of claim 40, further comprising an actuator configured to move said needle.

48. The access port system of claim 47, wherein said actuator is operable to apply an actuation force to move said needle.

49. The access port system of claim 47, wherein said actuator is operable in at least one of magnetic, mechanical and electrical communication with said needle.

50. The access port system of claim 47, wherein said actuator is configured to move said needle from said retracted position to said extended position.

51. The access port system of claim 47, wherein said actuator is configured to move said needle from said extended position to said retracted position.

52. The access port system of claim 47, wherein said needle is configured to be extended from within said access port body by said actuator.

53. The access port system of claim 47, wherein said needle is configured to be retracted into said access port body by said actuator.

54. The access port system of claim 47, wherein said actuator is outside said access port.

55. The access port system of claim 47, wherein said access port includes said actuator.

56. The access port system of claim 55, wherein said actuator is at least partially contained within said access port body of said access port.

57. The access port system of claim 56, wherein said actuator is completely contained within said access port body of said access port.

58. The access port system of claim 47, wherein said actuator comprises a magnetic actuator.

59. The access port system of claim 58, wherein said magnetic actuator comprises at least one magnet configured to move said needle with a magnetic force.

60. The access port system of claim 47, wherein said actuator comprises a mechanical actuator.

61. The access port system of claim 60, wherein said mechanical actuator comprises at least one of a mechanical linkage, a lever, a spring, a pivot point and a push button.

62. The access port system of claim 61, wherein said spring comprises a coil spring.

63. The access port system of claim 1, wherein said spring is configured to move said needle towards said retracted position.

64. The access port system of claim 47, wherein said actuator comprises an electrical actuator.

65. The access port system of claim 64, wherein said electrical actuator comprises at least one of a motor, a linear traveler, a processor, a memory, a communication device, a transmitter, a receiver, a transceiver and a power supply.

66. The access port system of claim 47, wherein said actuator comprises a wireless electrical actuator which communicates wirelessly with said access port.

67. The access port system of claim 40, wherein said access port includes a mechanism to lock said needle in said extended position.

* * * * *